(12) United States Patent
Ho et al.

(10) Patent No.: US 12,005,090 B2
(45) Date of Patent: *Jun. 11, 2024

(54) PROBIOTIC COMPOSITION INCLUDING LACTIC ACID BACTERIAL STRAINS AND USE OF AT LEAST ONE OF SUCH STRAINS

(71) Applicant: GLAC BIOTECH CO., LTD., Tainan (TW)

(72) Inventors: Hsieh-Hsun Ho, Tainan (TW); Ching-Wei Chen, Tainan (TW); Yu-Fen Huang, Tainan (TW); Yi-Wei Kuo, Tainan (TW); Wen-Yang Lin, Tainan (TW); Yen-Yu Huang, Tainan (TW)

(73) Assignee: GLAC BIOTECH CO., LTD., Tainan (TW)

( * ) Notice: Subject to any disclaimer, the term of this patent is extended or adjusted under 35 U.S.C. 154(b) by 0 days.

This patent is subject to a terminal disclaimer.

(21) Appl. No.: 17/449,699

(22) Filed: Oct. 1, 2021

(65) Prior Publication Data

US 2022/0265736 A1 Aug. 25, 2022

(30) Foreign Application Priority Data

Feb. 19, 2021 (TW) ................. 110105666

(51) Int. Cl.
*A61K 35/747* (2015.01)
*A23L 33/135* (2016.01)
*A61K 35/745* (2015.01)
*A61P 3/04* (2006.01)

(52) U.S. Cl.
CPC .......... *A61K 35/747* (2013.01); *A23L 33/135* (2016.08); *A61K 35/745* (2013.01); *A61P 3/04* (2018.01)

(58) Field of Classification Search
CPC ........ A23L 33/135; A61K 35/745; A61P 3/04
USPC ....................................... 424/93.45
See application file for complete search history.

(56) References Cited

U.S. PATENT DOCUMENTS

2011/0268715 A1* 11/2011 Hsieh ................. A61K 35/747
424/93.45
2021/0275612 A1* 9/2021 Liu ....................... A23L 33/135

FOREIGN PATENT DOCUMENTS

CN 106389763 * 2/2017

OTHER PUBLICATIONS

Huang et al., Exercise Training Combined with Bifidobacterium Longum OLP-01 Supplementation Improves Exercise Physiological Adaption and Performance, Nutrients, (Apr. 19, 2020), 12, 1145, pp. 1-16.*

* cited by examiner

*Primary Examiner* — Jennifer M. H. Tichy
(74) *Attorney, Agent, or Firm* — Nixon & Vanderhye, P.C.

(57) ABSTRACT

Disclosed herein is a probiotic composition including *Lactobacillus salivarius* subsp. *salicinius* AP-32 that is deposited at the China Center for Type Culture Collection (CCTCC) under an accession number CCTCC M 2011127, and *Bifidobacterium longum* subsp. *longum* OLP-01 that is deposited at the China General Microbiological Culture Collection Center (CGMCC) under an accession number CGMCC 17345. Also disclosed herein are use of at least one of the abovementioned lactic acid bacterial strains for treating obesity and/or an obesity-related disorder, and for inhibiting fat absorption.

10 Claims, 4 Drawing Sheets

PROBIOTIC COMPOSITION INCLUDING LACTIC ACID BACTERIAL STRAINS AND USE OF AT LEAST ONE OF SUCH STRAINS

CROSS-REFERENCE TO RELATED APPLICATION

This application claims priority of Taiwanese Invention Patent Application No. 110105666, filed on Feb. 19, 2021.

FIELD

The present disclosure relates to a probiotic composition including two lactic acid bacterial strains. The present disclosure also relates to use of at least one of such strains for treating obesity and/or an obesity-related disorder and for inhibiting fat absorption.

BACKGROUND

When a human body consumes an excessive amount of food and lacks physical exercise, excessive calories are mainly stored in adipose tissues as body fat which includes visceral fat. Accumulation of excessive body fat which cannot be metabolized normally would cause obesity and lead to an obesity-related disorder, including hypertension, cardiovascular diseases, fatty liver diseases, arthritis, cancer, etc. As such, approaches related to reduction of body fat and body weight have received much attention in recent years.

In addition to dietary restriction and increased physical activity, a conventional method for treating obesity and an obesity-related disorder includes use of anti-obesity medication such as sibutramine (brand name: Meridia®) among others) to suppress appetite or orlistat (brand name: Xenical®) among others) to inhibit fat absorption from diet. However, long-term use of these anti-obesity drugs not only fails to achieve the desired effect, but also causes patients to suffer from serious side effects and adverse effects. Therefore, those skilled in the art still strive to develop drugs that can effectively treat obesity and obesity-related diseases without causing undesirable effects.

Lactic acid bacteria (LAB) are gram-positive, lactic acid-producing bacteria that are conferred with the generally recognized as safe (GRAS) status, and are widely used as probiotics. Examples of common LAB include *Lactobacillus* spp., *Lactococcus* spp., *Pediococcus* spp., *Streptococcus* spp., *Enterococcus* spp., *Bifidobacterium* spp., *Bacillus* spp., *Leuconostoc* spp., etc.

Previous studies demonstrated that certain strains of LAB have anti-obesity activity. As retrospectively reviewed in Sivamaruthi B. S. et al. (2019), *BioMed. Res. Int.*, 2019: 3291367, obese pregnant women supplemented with a single probiotic strain of *Lactobacillus salivarius* UCC118 showed reduced body mass index (BMI) while obese pregnant women supplemented with Vivomixx® (i.e., a mixture of probiotics including *Bifidobacterium infantis* DSM 24737, *Streptococcus thermophilus* DSM 24731, and *Lactobacillus acidophilus* DSM 24735) showed significant reduction in weight gain during the pregnancy period. On the other hand, Sivamaruthi B. S. et al. also disclosed that, as reported in a previous study, a mixture of probiotic strains including several *Bifidobacterium* spp. (including *Bifidobacterium longum*) and *Lactobacillus* spp. (including *Lactobacillus acidophilus*) showed a clear reduction in energy intake despite no significant improvement in waist circumference and body mass, suggesting that such probiotic mixture can be used in dietary management for weight loss program.

As reported in Hsieh P. S. et al. (2020), *BMJ Open Diab. Res. Care*, 8:e001028, C57BL/6J-db/db diabetic mice administered with *Lactobacillus salivarius* AP-32, *Lactobacillus reuteri* GL-104, or a combination thereof showed a significant decrease in fasting blood glucose levels, and an improved glucose tolerance and blood lipid profiles despite showing no significant change in body weight.

In spite of the aforesaid, those skilled in the art still strive to develop an efficient and effective way for treating obesity and/or an obesity-related disorder.

SUMMARY

Therefore, in a first aspect, the present disclosure provides a probiotic composition which can alleviate at least one of the drawbacks of the prior art.

The probiotic composition includes *Lactobacillus salivarius* subsp. *salicinius* AP-32 which is deposited at the China Center for Type Culture Collection (CCTCC) under an accession number CCTCC M 2011127, and *Bifidobacterium longum* subsp. *longum* OLP-01 which is deposited at the China General Microbiological Culture Collection Center (CGMCC) under an accession number CGMCC 17345.

In a second aspect, the present disclosure provides a method for treating obesity and/or an obesity-related disorder, which can alleviate at least one of the drawbacks of the prior art, and which includes administering to a subject in need thereof a pharmaceutical composition containing at least one lactic acid bacterial strain selected from the group consisting of the abovementioned *Lactobacillus salivarius* subsp. *salicinius* AP-32 and *Bifidobacterium longum* subsp. *longum* OLP-01.

In a third aspect, the present disclosure provides a method for inhibiting fat absorption, which can alleviate at least one of the drawbacks of the prior art, and which includes administering to a subject in need thereof a probiotic composition containing at least one lactic acid bacterial strain selected from the group consisting of the abovementioned *Lactobacillus salivarius* subsp. *salicinius* AP-32 and *Bifidobacterium longum* subsp. *longum* OLP-01.

BRIEF DESCRIPTION OF THE DRAWINGS

Other features and advantages of the present disclosure will become apparent in the following detailed description of the embodiments with reference to the accompanying drawings, of which.

DETAILED DESCRIPTION

Figure 1:
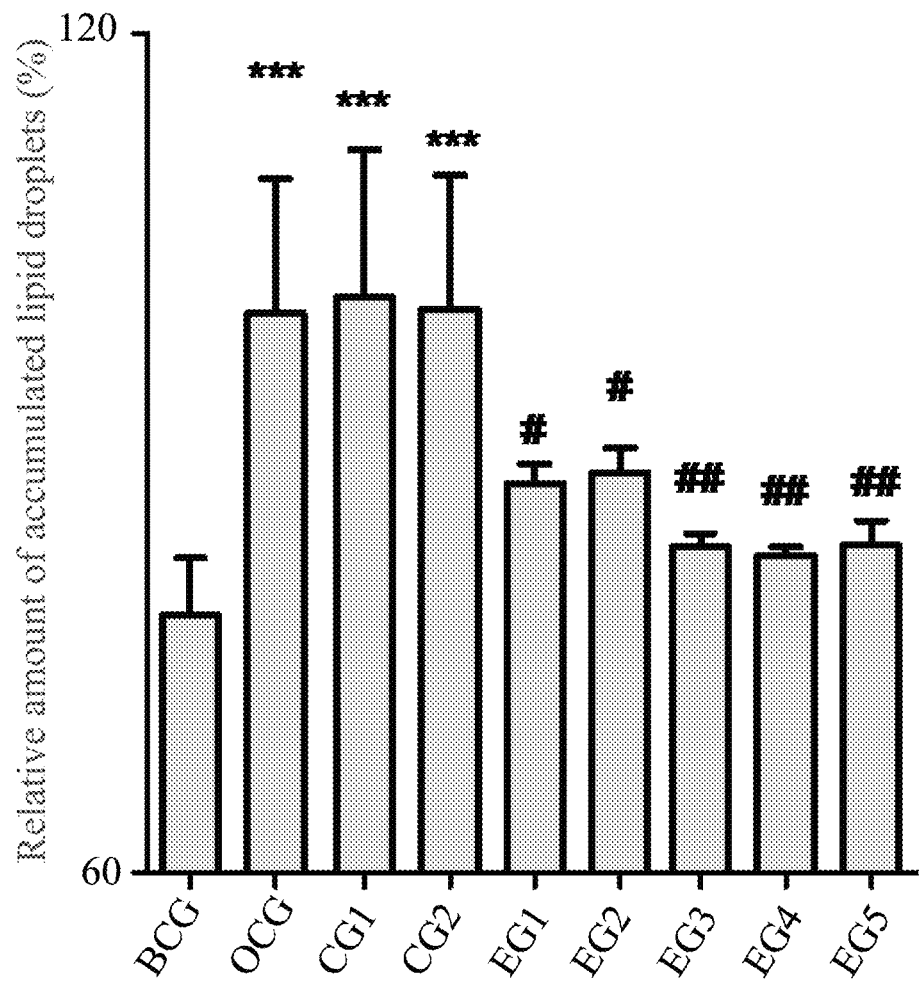
FIG. 1 shows the relative amount of accumulated oil droplets in Caco-2 cells in each group of Example 1, infra, in which the symbol "***" represents $p<0.001$ compared with the blank control group (BCG), the symbol "#" represents $p<0.05$ compared with the oleic acid control group (OCG), and the symbol "##" represents $p<0.01$ compared with the OCG.

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless otherwise defined, all technical and scientific terms used herein have the meaning commonly understood by a person skilled in the art to which this disclosure belongs. One skilled in the art will recognize many methods and materials similar or equivalent to those described herein, which could be used in the practice of this disclosure. Indeed, this disclosure is in no way limited to the methods and materials described.

In the development of drugs that can be used to treat obesity and/or obesity-related disorders, the applicant surprisingly found that *Lactobacillus salivarius* subsp. *salicinius* AP-32 and *Bifidobacterium longum* subsp. *longum* OLP-01 are capable of effectively inhibiting absorption of fatty acids by human intestinal epithelial cells and reducing formation of body fat, and a combination of these lactic acid bacterial strains demonstrates synergistic improved efficacy. Thus, these lactic acid bacterial strains are expected to be effective in treating obesity and/or obesity-related disorders.

Therefore, the present disclosure provides a probiotic composition, which includes *Lactobacillus salivarius* subsp. *salicinius* AP-32 which is deposited at the China Center for Type Culture Collection (CCTCC) under an accession number CCTCC M 2011127, and *Bifidobacterium longum* subsp. *longum* OLP-01 which is deposited at the China General Microbiological Culture Collection Center (CGMCC) under an accession number CGMCC 17345.

According to the present disclosure, the obesity-related disorder to be treated with the two aforesaid lactic acid bacterial strains may be selected from the group consisting of hypertension, atherosclerosis, a cardiovascular disease, a fatty liver disease, and combinations thereof. Examples of the cardiovascular disease include, but are not limited to, coronary artery disease, acute myocardial infarction, stroke, heart failure, cardiac arrhythmias, and hypertensive heart disease. Examples of the fatty liver disease (also known as hepatic steatosis) include, but are not limited to, acute fatty liver, chronic fatty liver, macrovesicular fatty liver, microvesicular fatty liver, and non-alcoholic steatohepatitis.

According to the present disclosure, a ratio of a number of *Lactobacillus salivarius* subsp. *salicinius* AP-32 to that of *Bifidobacterium longum* subsp. *longum* OLP-01 ranges from 1:0.2 to 1:5. In an exemplary embodiment, a ratio of the number of *Lactobacillus salivarius* subsp. *salicinius* AP-32 to that of *Bifidobacterium longum* subsp. *longum* OLP-01 is 1:1.

According to the present disclosure, the probiotic composition may have a bacterial concentration ranging from $10^5$ CFU/g to $10^{12}$ CFU/g. In an exemplary embodiment, the composition has a bacterial concentration ranging from $10^9$ CFU/g to $10^{10}$ CFU/g.

According to the present disclosure, *Lactobacillus salivarius* subsp. *salicinius* AP-32 and *Bifidobacterium longum* subsp. *longum* OLP-01 may be live cells or dead cells, concentrated or non-concentrated, a liquid, a paste, a semi-solid, a solid (e.g., a pellet, a granule, or a powder), and may be heat-inactivated, frozen, dried, or freeze-dried (e.g., may be in a freeze-dried form or spray/fluid bed dried form). In an exemplary embodiment, *Lactobacillus salivarius* subsp. *salicinius* AP-32 and *Bifidobacterium longum* subsp. *longum* OLP-01 are in a freeze-dried form.

In certain embodiments, the probiotic composition of the present disclosure may be formulated as a food product using a standard technique well known to one of ordinary skill in the art. For example, the composition may be directly added to an edible material or may be used to prepare an intermediate composition (e.g., a premix) suitable to be subsequently added to the edible material.

As used herein, the term "food product" refers to any article or substance that can be ingested by a subject into the body thereof. Examples of the food product may include, but are not limited to, fluid milk products (e.g., milk and concentrated milk), fermented milk (e.g., yogurt, sour milk, and frozen yogurt), milk powder, ice cream, cream cheese, dry cheese, soybean milk, fermented soybean milk, vegetable fruit juice, fruit juice, sport drinks, confectionery, jelly, candies, health foods, animal feeds, feed additives, and dietary supplements.

In certain embodiments, the probiotic composition of the present disclosure may be formulated as a pharmaceutical composition. The pharmaceutical composition may further include a pharmaceutically acceptable carrier, and may be made into a dosage form suitable for oral administration or topical administration using technology well-known to those skilled in the art.

Examples of the pharmaceutically acceptable carrier may include, but are not limited to, solvents, buffers, emulsifiers, suspending agents, decomposers, disintegrating agents, dispersing agents, binding agents, excipients, stabilizing agents, chelating agents, diluents, gelling agents, preservatives, wetting agents, lubricants, absorption delaying agents, liposomes, and the like. The choice and amount of the pharmaceutically acceptable carrier are within the expertise of those skilled in the art.

Examples of the dosage form for oral administration include, but are not limited to, sterile powder, tablets, troches, lozenges, pellets, capsules, dispersible powder, granule, solutions, suspensions, emulsions, drops, syrup, elixirs, slurry, and the like.

Examples of the dosage form for topical administration to the skin (i.e., manufactured as an external preparation) include, but are not limited to, emulsions, gels, ointments, creams, patches, serums, pastes, foams, drops, suspensions, salves, and bandages.

As used herein, the term "treating" or "treatment" means preventing, reducing, alleviating, ameliorating, relieving, or controlling one or more clinical signs of a disease or disorder, and lowering, stopping or reversing the progression of the severity of the condition(s) or symptom(s) that is being treated.

As used herein, the term "obesity" refers to a disease, disorder or condition associated with an increase in body weight and body fat in a subject (a human, in particular) which is caused by abnormal or excessive accumulation of body fat (i.e., adipose tissue mass).

As used herein, the term "treating obesity" can be used interchangeably with the terms "anti-obesity", "losing weight", and "weight loss", and is intended to refer to inhibiting fat absorption, inhibiting the formation and accumulation of body fat (i.e., including visceral fat) and reducing body fat.

The present disclosure also provides a method for treating obesity and/or an obesity-related disorder, which includes administering to a subject in need thereof a pharmaceutical composition containing at least one lactic acid bacterial strain selected from the group consisting of the aforesaid *Lactobacillus salivarius* subsp. *salicinius* AP-32 and *Bifidobacterium longum* subsp. *longum* OLP-01. The details regarding the pharmaceutical composition applied in this method, which contains both or either one of the aforesaid two lactic acid bacterial strains, is generally the same as that described above for the pharmaceutical composition containing both of the aforesaid two lactic acid bacterial strains.

As used herein, the term "administering" or "administration" means introducing, providing or delivering a predetermined active ingredient to a subject by any suitable routes to perform its intended function.

As used herein, the term "subject" refers to any animal of interest, such as humans, monkeys, cows, sheep, horses, pigs, goats, dogs, cats, mice, and rats. In certain embodiments, the subject is a human.

Furthermore, the aforesaid *Lactobacillus salivarius* subsp. *salicinius* AP-32 and *Bifidobacterium longum* subsp. *longum* OLP-01 have been verified to effectively inhibit fat absorption through in vivo animal testing. As such, it is contemplated that the aforesaid two lactic acid bacterial strains, can be used for inhibiting fat absorption.

Therefore, the present disclosure further provides a method for inhibiting fat absorption, which includes administering to a subject in need thereof a probiotic composition containing at least one lactic acid bacterial strain selected from the group consisting of the aforesaid *Lactobacillus salivarius* subsp. *salicinius* AP-32 and *Bifidobacterium longum* subsp. *longum* OLP-01. The details regarding the probiotic composition applied in this method, which contains both or either one of the aforesaid two lactic acid bacterial strains, is generally the same as that described above for the probiotic composition containing both of the aforesaid two lactic acid bacterial strains.

The dose and frequency of administration of the composition of the present disclosure may vary depending on the following factors: the severity of the illness or disorder to be treated, routes of administration, and age, physical condition and response of the subject to be treated. In general, the composition may be administered in a single dose or in several doses.

The present disclosure will be further described by way of the following examples. However, it should be understood that the following examples are intended solely for the purpose of illustration and should not be construed as limiting the present disclosure in practice.

EXAMPLES

General Experimental Materials

1. Lactic Acid Bacterial (LAB) Strains

A. *Lactobacillus salivarius* subsp. *salicinius* AP-32

*Lactobacillus salivarius* subsp. *salicinius* AP-32, which is disclosed in the applicant's previous Taiwanese Invention Patent Publication No. 1542353, has been deposited at the Biosource Collection and Research Center (BCRC) of the Food Industry Research and Development Institute (FIRDI) (No. 331, Shih-Pin Rd., Hsinchu City 300, Taiwan) under an accession number BCRC 910437 since Jul. 30, 2009, and has also been deposited at the China Center for Type Culture Collection (CCTCC) of Wuhan University, the College of Life Sciences (No. 299, Bayi Rd., Wuchang District, Wuhan City 430072, Hubei Province, China) under an accession number CCTCC M 2011127 since Apr. 10, 2011.

B. *Bifidobacterium longum* subsp. *longum* OLP-01

*Bifidobacterium longum* subsp. *longum* OLP-01, which is disclosed in the applicant's previous U.S. Patent Application Publication No. US 2021/0052676 A1, has been deposited at the BCRC of the FIRDI under an accession number BCRC 910875 since Feb. 22, 2019, and has also been deposited at the China General Microbiological Culture Collection Center (CGMCC) of Chinese Academy of Sciences, the Institute of Microbiology (No. 1, West Beichen Rd., Chaoyang District, Beijing 100101, China) under an accession number CGMCC 17345 since Mar. 18, 2019.

C. *Lactobacillus salivarius* L-331

*Lactobacillus salivarius* L-331 used in the following experiments was isolated from the feces of a healthy subject by the applicant.

D. *Bifidobacterium animalis* subsp. *lactis* L-39

*Bifidobacterium animalis* subsp. *lactis* L-39 used in the following experiments was isolated from the breast milk of a healthy subject by the applicant.

Prior to use in the following experiments, a respective one of the aforesaid LAB strains was inoculated into 5 mL of a BD Difco™ Lactobacilli MRS (De Man, Rogosa and Sharpe) broth (Catalogue no.: DF0881-17-5) supplemented with 0.05% (w/w) cysteine, and was then cultured at a temperature of 37° C. for 18 hours to obtain a respective one of LAB inoculums, followed by culturing the LAB inoculums at the aforesaid conditions, thereby activating the cells of a respective one of the four LAB strains.

2. Source and Cultivation of Human Colon Adenocarcinoma Cell Line Caco-2

Human colon adenocarcinoma cell line Caco-2 (ATCC® HTB-37™) used in the following experiments was purchased from American Type Culture Collection (ATCC, Manassas, VA, USA). The Caco-2 cells were incubated in a 10-cm Petri dish containing Gibco Dulbecco's modified Eagle's medium (DMEM)(Thermo Fisher Scientific) supplemented with 10% fetal bovine serum (FBS), followed by cultivation in an incubator with culture conditions set at 37° C. and 5% $CO_2$. Medium change was performed every 3 to 5 days. When reaching 80% to 90% of confluence, the cultured cells were washed with phosphate-bufffered saline (PBS)(pH 7.4), and were then detached from the bottom of the Petri dish using trypsin-EDTA, followed by adding a fresh DMEM medium containing 10% FBS to neutralize trypsin activity and then resuspending the cells in the DMEM medium using a pipette so as to fully disperse the cells. The resulting cell suspensions were distributed to new Petri dishes to be incubated at the aforesaid culture conditions.

3. Experimental Mice

Male ICR (Institute of Cancer Research) mice (8 weeks old, with a body weight of approximately 30 g) used in the following experiments were purchased from BioLasco Taiwan Co., Ltd. All the experimental mice were housed in an animal room with an independent air conditioning system under the following laboratory conditions: an alternating 12-hour light and 12-hour dark cycle, a temperature maintained at 24° C.±2° C., and a relative humidity maintained at 60% to 70%. The mice were provided with water and fed ad libitum. All experimental procedures involving the experimental mice were in compliance with the legal provision of the Animal Protection Act of Taiwan, and were carried out according to the guidelines of the Animal Care Committee of the Council of Agriculture, Taiwan.

General Procedures:

1. Statistical analysis

All the experiments described below were performed in triplicates. The experimental data of all the test groups are expressed as mean±standard deviation (SD), and were analyzed using two-tailed Student's t-test using GraphPad Prism 5 software (Developer: GraphPad Sofware, Inc., San Diego, CA), so as to assess the differences between the groups. Statistical significance is indicated by $p<0.05$.

Example 1. Evaluation of the Effect of *Lactobacillus salivarius* Subsp. *salicinius* AP-32 and *Bifidobacterium longum* Subsp. *longum* OLP-01 on the Inhibition of Fatty Acid Absorption In order to evaluate the efficacy of *Lactobacillus salivarius* subsp. *salicinius* AP-32 and *Bifidobacterium longum* subsp. *longum* OLP-01 on the inhibition of fatty acid absorption by intestinal epithelial cells, the following experiments were conducted.

Experimental Materials:

A. Preparation of Bacterial Suspension of LAB Strain

A respective one of the four LAB strains as described in the section entitled "1. Lactic acid bacterial (LAB) strains" of the General Experimental Materials was inoculated into 5 mL of a Lactobacilli MRS broth, and was then cultured at a temperature of 37° C. for 18 hours to obtain a respective one of LAB cultures. Next, each of the LAB cultures was subjected to centrifugation at 4° C. under a speed of 3,000 rpm for 5 minutes to form supernatant and pellet fractions. After that, the supernatant was poured off, and then the pellet was washed with an appropriate amount of PBS, followed by resuspending the pellet in an appropriate amount of DMEM supplemented with 2% bovine serum albumin (BSA) and 500 µM of oleic acid (Manufacturer: Sigma-Aldrich; Catalogue No: O1383), so as to obtain a bacterial suspension having a bacterial concentration of $2\times10^8$ CFU/mL, which was determined using a plate counting medium (Manufacturer: BD Difco™, USA). The respective one of the resultant bacterial suspensions was used for the following experiments.

Experimental Procedures:

A. Treatment of Caco-2 Cells Using Bacterial Suspension of LAB Strain

The Caco-2 cells as described in the section entitled "2. Source and cultivation of human colon adenocarcinoma cell line Caco-2" of the General Experimental Materials were seeded at a concentration of $2\times10^6$ cells per well into respective wells of 6-well plates each containing 3 mL of DMEM supplemented with 10% FBS, 1% (v/v) penicillin-steptomycin (Manufacturer: GE Healthcare Life Sciences; Catalogue No.: SV30010), and 0.01 mg/mL human transferrin (Manufacturer: Sigma-Aldrich; Catalogue No.: T8158), and then were divided into 9 groups, namely, a blank control group (BCG), an oleic acid control group (OCG), two comparative groups (i.e., comparative group 1 (CG1) and comparative group 2 (CG2)), and five experimental groups (i.e., experimental group 1 (EG1), experimental group 2 (EG2), experimental group 3 (EG3), experimental group 4 (EG4) and experimental group 5 (EG5)).

After culturing for 6 hours at 37° C. and 5% $CO_2$, each of the cell cultures of the CG1, CG2, EG1, EG2, EG3, EG4 and EG5 was treated with the respective one of the bacterial suspensions prepared in the section entitled "A. Preparation of bacterial suspension of LAB strain" of the Experimental Materials, as shown in Table 1 below. In addition, the cell culture of the OCG was treated with 500 µM oleic acid only, while the cell culture of the BCG received no treatment.

TABLE 1

| | Treating agent (mL) | | | |
|---|---|---|---|---|
| Group | Bacterial suspension of *Lactobacillus salivarius* subsp. *salicinius* AP-32 | Bacterial suspension of *Bifidobacterium longum* subsp. *longum* OLP-01 | Bacterial suspension of *Lactobacillus salivarius* L-331 | Bacterial suspension of *Bifidobacterium animalis* subsp. *lactis* L-39 |
| CG1 | — | — | 2 | — |
| CG2 | — | — | — | 2 |
| EG1 | 2 | — | — | — |
| EG2 | — | 2 | — | — |
| EG3 | 1 | 1 | — | — |
| EG4 | 1.33 | 0.67 | — | — |
| EG5 | 0.67 | 1.33 | — | — |

B. Determination of Relative Amount of Accumulated Lipid Droplets

After performing the aforesaid incubation, the culture medium in each group was removed, and 1 mL of a 10% (v/v) aqueous formaldehyde solution was added to fix the cells at 37° C. for 10 minutes, followed by washing with appropriate amount of PBS. Subsequently, 1 mL of an Oil-Red-O solution (Manufacturer: Sigma-Aldrich; CAS No.: 1320-06-5) was added to stain the accumulated lipid droplets in the cells at 37° C. for 15 minutes. After rinsing with PBS, the stained cells were added with 1 mL of isopropanol and left to stand at 25° C. for 10 minutes, and were then subjected to light absorbance measurement at a wavelength of 520 nm ($OD_{520}$) using a spectrophotometer (Manufacturer: Eppendorf; Model No.: BioPhotometer® D30).

The relative amount of accumulated lipid droplets in the Caco-2 cells of each group was determined as the percentage of the light absorbance value ($OD_{520}$ of the Caco-2 cells of the respective group relative to the $OD_{520}$ of the Caco-2 cells of the OCG, and the differences thereof were analyzed according to the procedures as described in the section of the General Procedures, entitled "1. Statistical analysis".

Results:

FIG. 1 shows the relative amount of accumulated lipid droplets in the Caco-2 cells in each group. As shown in FIG. 1, the relative amount of accumulated lipid droplets determined in the OCG was significantly higher than that in the BCG, indicating that Caco-2 cells are capable of absorbing oleic acid from external environment for the same to be accumulated intracellularly. In addition, the relative amount of accumulated lipid droplets determined in each of the EG1 to EG5 was significantly reduced as compared with that of the OCG. It should be noted that, the relative amount of accumulated lipid droplets determined in the EG3, EG4 and EG5 was even similar to that of the BCG. On the contrary, no significant difference was observed on the relative amount of accumulated lipid droplets among the CG1, CG2, and OCG.

These results demonstrate that each of the *Lactobacillus salivarius* subsp. *salicinius* AP-32 and *Bifidobacterium longum* subsp. *longum* OLP-01 is capable of effectively inhibit the absorption of fatty acids/lipids by intestinal epithelial cells, and when used in combination, can synergistically exhibit a further improved efficacy. In contrast, each of *Lactobacillus salivarius* L-331 and *Bifidobacterium animalis* subsp. *lactis* L-39 cannot exert the aforesaid effect.

Example 2. Evaluation of the Effect of
*Lactobacillus salivarius* Subsp. *salicinius* AP-32
and *Bifidobacterium longum* Subsp. *longum*
OLP-01 on Alleviating Diet-Induced Obesity In this example, experimental mice were fed with a high energy diet (HED) to induce obesity, so as to evaluate in vivo therapeutic effect of *Lactobacillus salivarius* subsp. *salicinius* AP-32 and *Bifidobacterium longum* subsp. *longum* OLP-01.

A. Preparation of Bacterial Suspension of LAB Strain

The bacterial suspension of the respective one of *Lactobacillus salivarius* subsp. *salicinius* AP-32 and *Bifidobacterium longum* subsp. *longum* OLP-01 was prepared generally according to the procedures and conditions as described in the abovementioned section entitled "A. Preparation of bacterial suspension of LAB strain" of the Experimental Materials of Example 1, except for the following differences. The pellet fractions obtained after centrifugation of the cell culture of each of *Lactobacillus salivarius* subsp. *salicinius* AP-32 and *Bifidobacterium longum* subsp. *longum* OLP-01 were subjected to a freeze-drying process, and then the resultant freeze-dried *Lactobacillus salivarius* subsp. *salicinius* AP-32 powder and freeze-dried *Bifidobacterium longum* subsp. *longum* OLP-01 powder were resuspended in an appropriate amount of PBS, thereby obtaining the bacterial suspension of the respective one of *Lactobacillus salivarius* subsp. *salicinius* AP-32 and *Bifidobacterium longum* subsp. *longum* OLP-01 each having a concentration of $2.05 \times 10^8$ CFU/mL.

B. Induction of Obesity and Feeding of Bacterial Suspension of LAB Strain Via Oral Gavage The ICR mice as described in the section entitled "3. Experimental mice" of the General Experimental Materials were subjected to induction of obesity according to the guidelines "Health Care Effect Assessment: Reducing Body Fat Formation" of the Ministry of Health and Welfare, Taiwan, with slight modification.

The mice were randomly divided into a normal control group (NCG), a pathological control group (PCG), and two experimental groups (i.e., experimental group 1 (EG1) and experimental group 2 (EG2))(n=12 per each group). The mice in the NCG were fed ad libitum for a total of 8 weeks with a normal diet, i.e., LabDiet® Rodent Laboratory Chow 5001 (Manufacturer: Ralston Purina Co., MO, USA), and the mice in each of the PCG, EG1 and EG2 were fed ad libitum for a total of 8 weeks with a high energy diet (HED) containing 35% (w/w) lard (purchased from I-Mei Foods Co., Ltd., Taiwan), 15% (w/w) fructose syrup (purchased from Fonen and Fonher Enterprise Co., Ltd., Taiwan), and 0.2% (w/w) cholesterol (purchased from MP Biomedicals LLC, CA, USA).

On the first day after feeding the aforesaid diet to the mice in each group, the mice in the EG1 and EG2 were also respectively fed, via oral gavage, with the bacterial suspensions of *Lactobacillus salivarius* subsp. *salicinius* AP-32 and *Bifidobacterium longum* subsp. *longum* OLP-01 prepared in section A of this example, at a concentration of $2.05 \times 10^9$ CFU/kg per mouse. The mice in each of the NCG and PCG were fed, via oral gavage, with PBS at a volume of 5 mL. Each mouse was fed once daily for a total period of 8 weeks.

C. Determination of Body Weight

Prior to the feeding of the diet as described in section B of this example (i.e., at the $0^{th}$ week) and at the end of a respective one of the $2^{nd}$, $4^{th}$, $6^{th}$ and $8^{th}$ week after starting the feeding of the diet, the body weight of each mouse was measured. The data thus obtained were analyzed according to the procedures as described in the section of the General Procedures, entitled "1. Statistical analysis".

Figure 2:
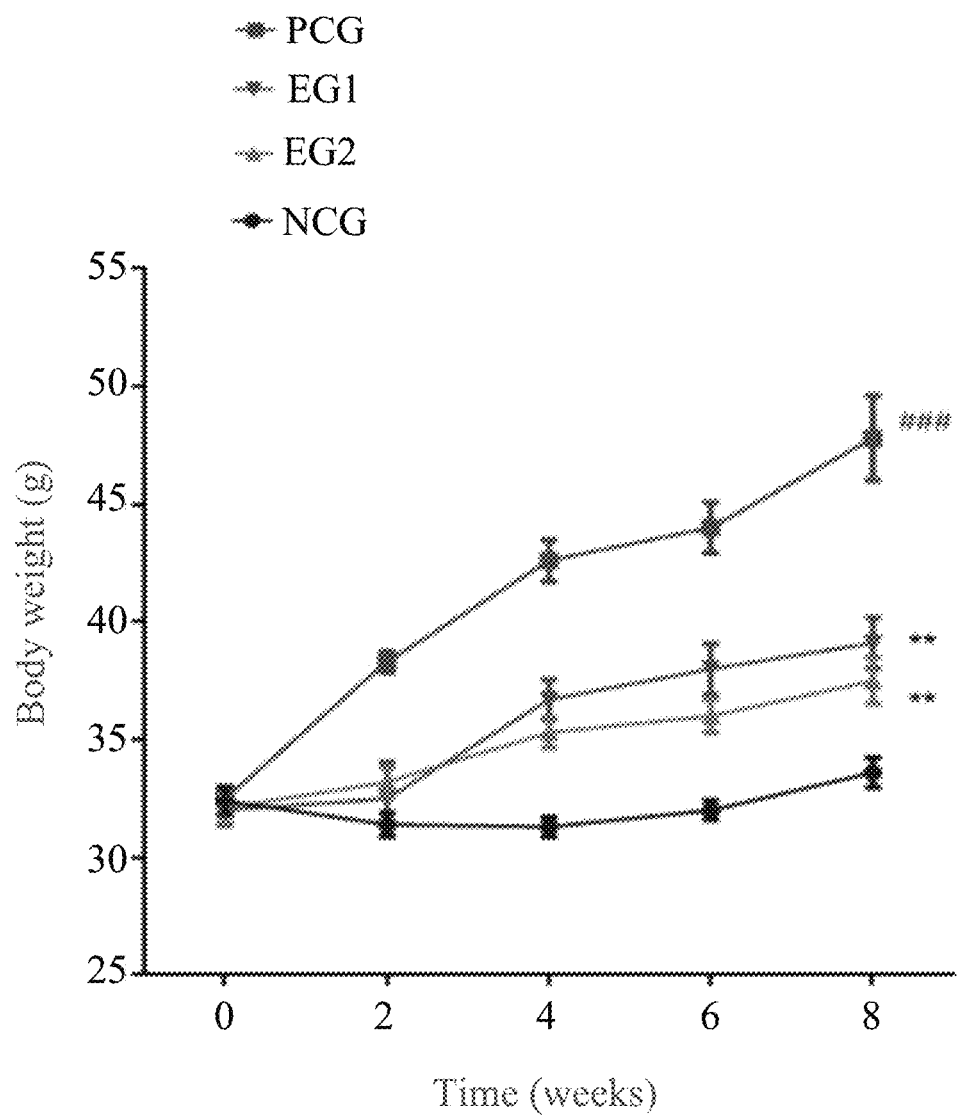
FIG. 2 shows the body weight of mice in each group of Example 2, infra, in which the symbol "###" represents $p<0.001$ compared with the normal control group (NCG), and the symbol "**" represents $p<0.01$ compared with the pathological control group (PCG)

Referring to FIG. 2, the body weight determined in the NCG was maintained at approximately 32.5 g for 8 weeks without significant changes, while the body weight determined in the PCG increased rapidly and significantly from the $0^{th}$ week to the end of the $8^{th}$ week, indicating that obesity was induced by feeding the HED to the mice in the PCG. In addition, in comparison with the PCG, the body weight determined in each of the EG1 and EG2 increased slowly from the $0^{th}$ week to the end of the 8th week, and such increase was significantly lower than that determined in the PCG.

D. Determination of Body Fat Percentage

After completion of the determination of body weight at the end of the $8^{th}$ week as described in section C of this example, the mice in each of the EG1, EG2, PCG, and NCG were sacrificed, and the epididymal fat, mesenteric fat, perirenal fat, and liver tissue were obtained from each mouse carcass. The epididymal fat, mesenteric fat, and perirenal fat of each mouse were subjected to weight measurement, so as to determine the body fat weight (i.e., the total weight of these three types of fat).

The body fat percentage of each mouse in a respective one of the EG1, EG2, PCG, and NCG was calculated by substituting the thus determined body fat weight and the body weight as obtained in section C of this example into the following formula:

$$A=(B/C) \times 100 \quad (1)$$

where A=body fat percentage (%)
B=body fat weight (g)
C=body weight (g)

The data thus obtained were analyzed according to the procedures as described in the section of the General Procedures, entitled "1. Statistical analysis".

Figure 3:
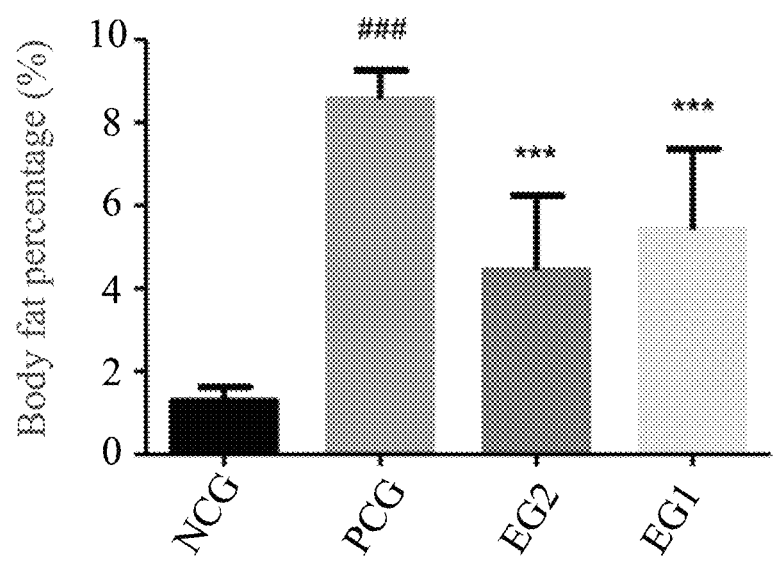
FIG. 3 shows the body fat percentage of the mice in each group of Example 2, infra, in which the symbol "###" represents $p<0.001$ compared with the NCG, and the symbol "*" represents $p<0.001$ compared with the PCG.

Referring to FIG. 3, at the end of the $8^{th}$ week, the body fat percentage determined in the PCG was significantly higher than that determined in the NCG, indicating that feeding the HED caused excessive accumulation of body fat in the mice in the PCG. In addition, at the end of the $8^{th}$ week, the body fat percentages determined in the EG1 and EG2 were significantly lower than that determined in the PCG.

E. Determination of Contents of Triglyceride (TG) and Cholesterol in Liver Tissue Approximately 3 g to 5 g of the liver tissue of each mouse obtained in section D of this example was subjected to determination of the contents of TG and cholesterol using an ELISA kit for TG (Manufacturer: Cloud-Clone Corp., Catalogue No.: CEB687Ge). The data thus obtained were analyzed according to the procedures as described in the section of the General Procedures, entitled "1. Statistical analysis".

Figure 4:
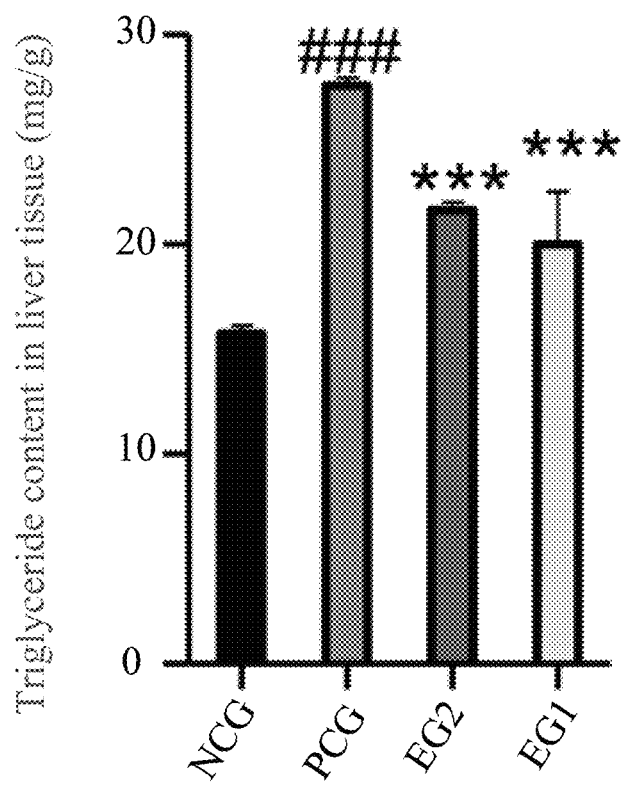
FIG. 4 shows the triglyceride (TG) content in the liver tissue of mice in each group of Example 2, infra, in which the symbol "###" represents p<0.001 compared with the NCG, and the symbol "*" represents p<0.001 compared with the PCG.

Referring to FIG. 4, at the end of the $8^{th}$ week, the liver TG content determined in the PCG was significantly higher than that determined in the NCG, indicating that feeding the HED caused excessive accumulation of triglyceride in the liver of the mice in the PCG. In addition, at the end of the 8th week, the liver TG contents determined in the EG1 and EG2 were significantly lower than that determined in the PCG.

Moreover, the liver cholesterol content determined in the PCG was significantly higher than that determined in the NCG, while the liver cholesterol contents determined in the EG1 and EG2 were significantly lower than that determined in the PCG (data not shown).

These results indicate that *Lactobacillus salivarius* subsp. *salicinius* AP-32 and *Bifidobacterium longum* subsp. *longum* OLP-01 can effectively reduce the body fat and body weight, and can reduce fat accumulation in liver tissues and ameliorate hepatic steatosis, and hence are expected to be useful for treating obesity and/or obesity-related disorders.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, is understood that this disclosure is not limited to the disclosed embodiments but is intended to cover various arrangements included within the spirit and scope of the broadest interpretation so as to encompass all such modifications and equivalent arrangements.

What is claimed is:

1. A method for treating obesity and/or an obesity-related disorder in a subject, the method comprising:
    administering to the subject in need thereof a pharmaceutical composition consisting of *Lactobacillus salivarius* subsp. *salicinius* AP-32 which is deposited at the China Center for Type Culture Collection (CCTCC) under an accession number CCTCC M 2011127, and *Bifidobacterium longum* subsp. *longum* OLP-01 which is deposited at the China General Microbiological Culture Collection Center (CGMCC) under an accession number CGMCC 17345,
    wherein a ratio of a number of *Lactobacillus salivarius* subsp. *salicinius* AP-32 to that of *Bifidobacterium longum* subsp. *longum* OLP-01 ranges from 1:0.5 to 1:2.

2. The method as claimed in claim 1, wherein the obesity-related disorder is selected from the group consisting of hypertension, atherosclerosis, a cardiovascular disease, a fatty liver disease, and combinations thereof.

3. The method as claimed in claim 1, wherein the pharmaceutical composition is in a dosage form for oral administration.

4. The method as claimed in claim 1, wherein the pharmaceutical composition is in a dosage form for topical administration.

5. The method as claimed in claim 1, wherein the ratio of the number of *Lactobacillus salivarius* subsp. *salicinius* AP-32 to that of *Bifidobacterium longum* subsp. *longum* OLP-01 is 1:1.

6. A method for inhibiting fat absorption in a subject, the method comprising:
    administering to the subject in need thereof a probiotic consisting of *Lactobacillus salivarius* subsp. *salicinius* AP-32 which is deposited at the China Center for Type Culture Collection (CCTCC) under an accession number CCTCC M 2011127, and *Bifidobacterium longum* subsp. *longum* OLP-01 which is deposited at the China General Microbiological Culture Collection Center (CGMCC) under an accession number CGMCC 17345,
    wherein a ratio of a number of *Lactobacillus salivarius* subsp. *salicinius* AP-32 to that of *Bifidobacterium longum* subsp. *longum* OLP-01 ranges from 1:0.5 to 1:2.

7. The method as claimed in claim 6, wherein the probiotic composition is a pharmaceutical composition in a dosage form for oral administration.

8. The method as claimed in claim 6, wherein the probiotic composition is a pharmaceutical composition in a dosage form for topical administration.

9. The method as claimed in claim 6, wherein the probiotic composition is a food product.

10. The method as claimed in claim 6, wherein the ratio of the number of *Lactobacillus salivarius* subsp. *salicinius* AP-32 to that of *Bifidobacterium longum* subsp. *longum* OLP-01 is 1:1.

* * * * *